US006331313B1

(12) United States Patent
Wong et al.

(10) Patent No.: US 6,331,313 B1
(45) Date of Patent: Dec. 18, 2001

(54) CONTROLLED-RELEASE BIOCOMPATIBLE OCULAR DRUG DELIVERY IMPLANT DEVICES AND METHODS

(75) Inventors: Vernon G. Wong, Menlo Park; Mae W. L. Hu, Los Altos Hills; Donald E. Berger, Jr., San Jose, all of CA (US)

(73) Assignee: Oculex Pharmaceticals, Inc., Sunnyvale, CA (US)

( * ) Notice: Subject to any disclaimer, the term of this patent is extended or adjusted under 35 U.S.C. 154(b) by 0 days.

(21) Appl. No.: 09/426,141

(22) Filed: Oct. 22, 1999

(51) Int. Cl.[7] .................................................... A61F 2/00
(52) U.S. Cl. ..................... 424/427; 424/422; 424/424; 424/423; 424/428; 604/891.1
(58) Field of Search .................................. 424/428, 422, 424/427, 424, 423; 604/891.1

(56) References Cited

U.S. PATENT DOCUMENTS

| 3,416,530 | 12/1968 | Ness . |
|---|---|---|
| 3,432,592 | 3/1969 | Speiser . |
| 3,845,770 | 11/1974 | Theeuwes et al. . |
| 3,916,899 | 11/1975 | Theeuwes et al. . |
| 3,921,632 | 11/1975 | Bardani . |
| 4,008,864 | 2/1977 | Torphammar et al. . |
| 4,063,064 | 12/1977 | Saunders et al. . |
| 4,088,864 | 5/1978 | Theeuwes et al. . |
| 4,144,317 | 3/1979 | Higuchi et al. . |
| 4,200,098 | 4/1980 | Ayer et al. . |
| 4,201,210 | 5/1982 | Hughes et al. . |
| 4,285,987 | 8/1981 | Ayer et al. . |
| 4,300,557 | 11/1981 | Refojo et al. . |
| 4,304,765 | 12/1981 | Shell et al. . |
| 4,451,254 | 5/1984 | Dinius et al. . |
| 4,668,506 | 5/1987 | Bawa . |
| 4,801,460 | 1/1989 | Goertz et al. . |
| 4,806,337 | 2/1989 | Snipes et al. . |
| 4,853,224 | 8/1989 | Wong . |
| 4,959,217 | 9/1990 | Sanders et al. . |
| 4,997,652 | 3/1991 | Wong . |

(List continued on next page.)

FOREIGN PATENT DOCUMENTS

| WO 94/18956 | 9/1994 | (WO) . |
|---|---|---|
| WO 94/11244 | 3/1999 | (WO) . |
| WO 94/62760 | 10/2000 | (WO) . |

OTHER PUBLICATIONS

Bundgaard, H. and Møss, J. (1989). "Prodrugs of Peptides IV: Bioreversible Derivatization of the Pyroglutamyl Group by N–Acylation and N–Aminomethylation to Effect Protection against Pyroglutamyl Aminopeptidase," *J. Pharm. Sci.* 78:122–126.

Cuff, G. and Raouf, F. (1998). "A Preliminary Evaluation of Injection Molding as a Technology to Produce Tablets," *Pharmaceutical Technology* pp. 96–106.

*Encyclopedia of Polymer Science and Technology* vol. 3. Interscience Publishers, Inc., New York (Table of Contents only).

(List continued on next page.)

Primary Examiner—Thurman K. Page
Assistant Examiner—Liliana Di Nola-Baron
(74) Attorney, Agent, or Firm—Morrison & Foerster LLP

(57) ABSTRACT

Controlled release devices are disclosed which are biocompatible and can be implanted into the eye. The devices have a core comprising a drug and a polymeric outer layer which is substantially impermeable to the entrance of an environmental fluid and substantially impermeable to the release of the drug during a delivery period, and drug release is effected through an orifice in the outer layer. These devices have an orifice area of less than 10% of the total surface area of the device and can be used to deliver a variety of drugs with varying degrees of solubility and or molecular weight. Methods are also provided for using these drug delivery devices.

19 Claims, 6 Drawing Sheets

U.S. PATENT DOCUMENTS

| | | |
|---|---|---|
| 5,004,601 | 4/1991 | Snipes . |
| 5,004,614 | 4/1991 | Staniforth . |
| 5,006,342 | 4/1991 | Cleary et al. . |
| 5,082,655 | 1/1992 | Snipes et al. . |
| 5,164,188 | 11/1992 | Wong . |
| 5,476,511 | 12/1995 | Gwon et al. . |
| 5,660,847 | 8/1997 | Magruder et al. . |
| 5,693,335 | 12/1997 | Xia et al. . |
| 5,824,072 | 10/1998 | Wong . |
| 5,824,074 | 10/1998 | Koch . |
| 5,869,079 * | 2/1999 | Wong et al. .......... 424/426 |
| 5,882,682 | 3/1999 | Rork et al. . |
| 5,972,369 * | 10/1999 | Roorda et al. .......... 424/424 |

OTHER PUBLICATIONS

Goodman and Gilman. *The Pharmacological Basis of Therapeutics,* 9th Edition. McGraw–Hill, New York (Table of Contents only).

Gennaro A. R., ed. (1995). *Remington: The Science and Practice of Pharmacy,* 19th Edition. Mack Publishing Company, Easton, PA (Table of Contents only).

Roff, W. J. and Scott, J. R. (1971). *Handbook of Common Polymers.* CRC Press, Cleveland, OH.

Budavari, S. et al., eds. (1996). *The Merck Index,* 12th Edition. Merck and Co., Rahway, N.J. (Table of Contents only).

*The United States Pharmacoepia,* USP 23, NF 18 (1994). The United States Pharmacopeial Convention, Inc., Rockville, MD.

* cited by examiner

FIG. 1  DRUG RELEASE FROM CYLINDRICAL DEVICES

CONTROLLED-RELEASE BIOCOMPATIBLE OCULAR DRUG DELIVERY IMPLANT DEVICES AND METHODS

TECHNICAL FIELD

The present invention relates to biocompatible controlled-release drug delivery devices that are implantable in the eye. Accordingly, the invention transcends the scientific disciplines of pharmaceutical delivery, polymer chemistry, and medicine.

BACKGROUND ART

A leading cause of blindness is the inability to introduce drugs or therapeutic agents into the eye and maintain these drugs or agents at a therapeutically effective concentration therein for the necessary duration. Systemic administration may not be an ideal solution because, often, unacceptably high levels of systemic dosing is needed to achieve effective intraocular concentrations, with the increased incidence of unacceptable side effects of the drugs. Simple ocular instillation or application is not an acceptable alternative in many cases because the drug may be quickly washed out by tear-action or is depleted from within the eye into the general circulation.

A better solution would be to provide a delivery device which can be implanted into the eye such that a controlled amount of desired drug can be released constantly over a period of several days, or weeks, or even months. Some such devices have been reported in the prior art. See, for example, U.S. Pat. No. 4,853,224, which discloses biocompatible implants for introduction into an anterior segment or posterior segment of an eye for the treatment of an ocular condition. U.S. Pat. No. 5,164,188 discloses a method of treating an ocular condition by introduction of a biodegradable implant comprising drugs of interest into the suprachoroidal space or pars plana of the eye. See also U.S. Pat. Nos. 5,824,072, 5,476,511, 4,997,652, 4,959,217, 4,668,506, and 4,144,317.

Many of the above-disclosed devices comprise of multiple layers and are complicated in their design and manufacture. Moreover, some of the devices are osmotically driven wherein an osmotic gradient is responsible for the drug efflux from the device. In some cases, the drug release is controlled by an ionic gradient. These devices thus must necessarily comprise these additional osmotic or ionic agents, which may not be compatible with the ocular environment. Thus, there is a need for a biocompatible ocular implantable controlled release drug delivery device that is simple in design, does not require an osmotic or ionic agent for drug efflux and yet accomplishes the objectives of prolonged and uninterrupted ocular drug delivery. This invention meets this need.

DISCLOSURE OF THE INVENTION

A biocompatible implantable ocular controlled release drug delivery device comprising a substantially impermeable polymeric outer layer covering a core which comprises the drug to be delivered, wherein said outer layer has one or more orifices, and said orifices in total having a surface area of less than 10 percent of the total surface area of said device.

The outer layer of the devices of this invention can be made biodegradable.

The devices of this invention can be used to deliver an antibiotic, an antiviral agent, an anti-fungal agent, an anti-cancer agent, an antiglaucoma agent, an antiinflammatory agent, an analgesic, an immunomodulatory agent, a macromolecule or a mixture thereof.

The present invention provides a biocompatible implantable ocular controlled release drug delivery device as described above wherein the outer layer comprises polytetrafluoroethylene, the core comprises gentamicin, cefazolin, or a mixture thereof, and the total area of orifices is less than 1 percent of the total surface area of the device.

The outer layer of the biocompatible implantable ocular controlled release drug delivery device as described above comprises polyfluorinated ethylenepropylene, and the core comprises dexamethasone, and the total area of orifices is less than 7 percent of the total surface area of the device.

The outer layer of the biocompatible implantable ocular controlled release drug delivery device described above comprises polytetrafluoroethylene, and the core comprises aldose reductase inhibitor, and the total area of orifices is less than 8 percent of the total surface area of the device.

Also provided is a biocompatible implantable ocular controlled release drug delivery device as described above wherein the outer layer comprises polytetrafluoroethylene, or silicone or a mixture thereof, the core comprises ganciclovir[9-[[2-hydroxy-1-(hydroxymethyl)ethoxy]-methyl]-guanine], and the total area of orifices is less than 1 percent of the total surface area of the device.

Also provided is a biocompatible implantable ocular controlled release drug delivery device as described above wherein the outer layer comprises polylactic acid, polyglycolic acid, or a mixture thereof, the core comprises ganciclovir[9-[[2-hydroxy-1-(hydroxymethyl)ethoxy]-methyl]-guanine], and the the total area of orifices is less than 1 percent of the total surface area of the device.

Methods are also provided for administering the biocompatible implantable ocular controlled release drug delivery device.

MODES FOR CARRYING OUT THE INVENTION

A. General Techniques

Figure 1A:
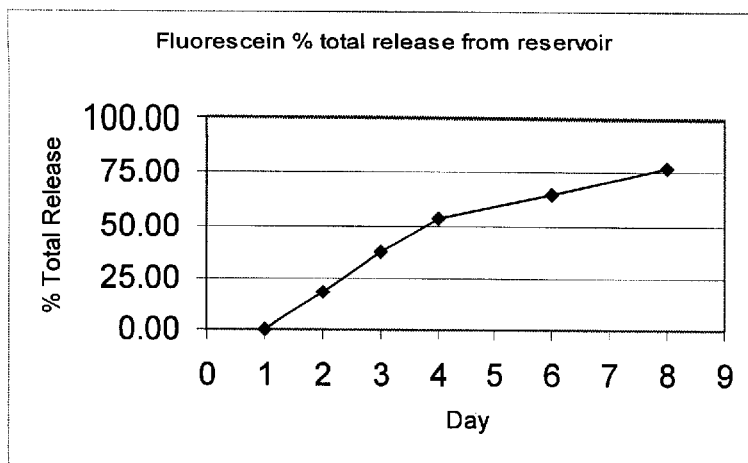
FIGS. 1A–1F are graphical displays of drug release data from cylindrical devices made from Teflon® (polytetrafluoroethylene), wherein the number and configuration of orifices varied.
Figure 1B:
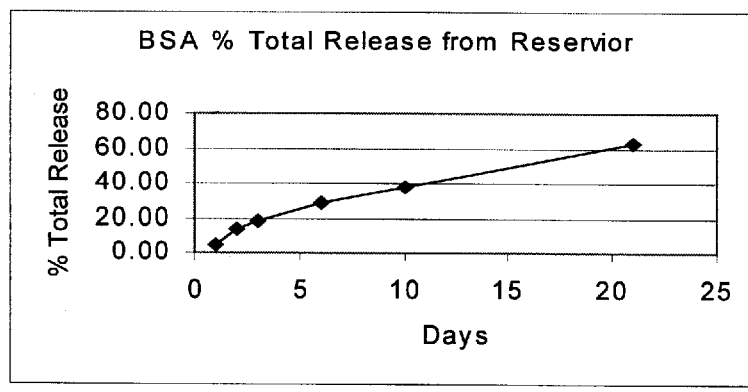
Figure 1C:
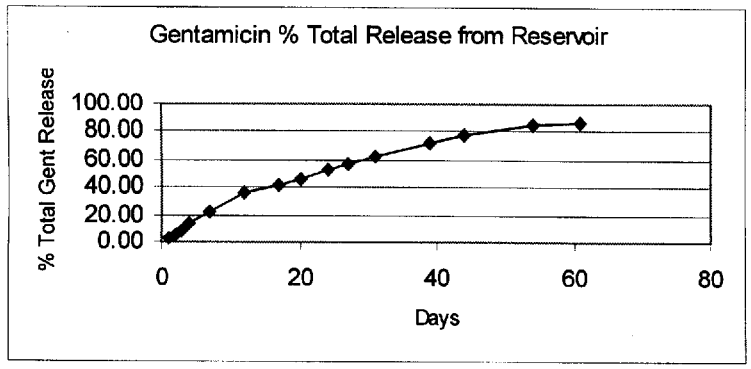
Figure 1D:
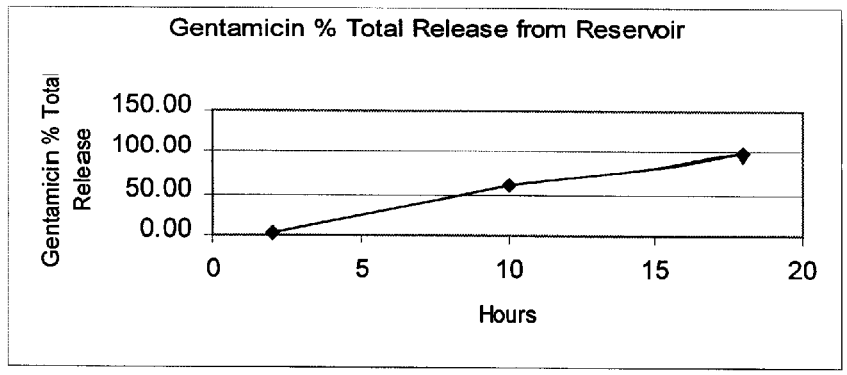
Figure 1E:
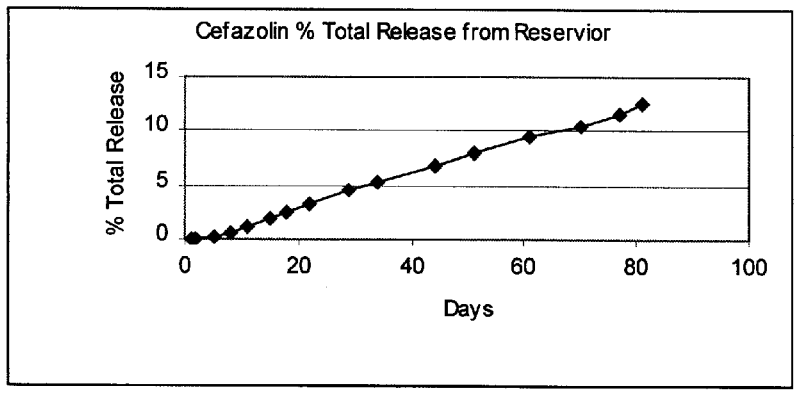
Figure 1F:
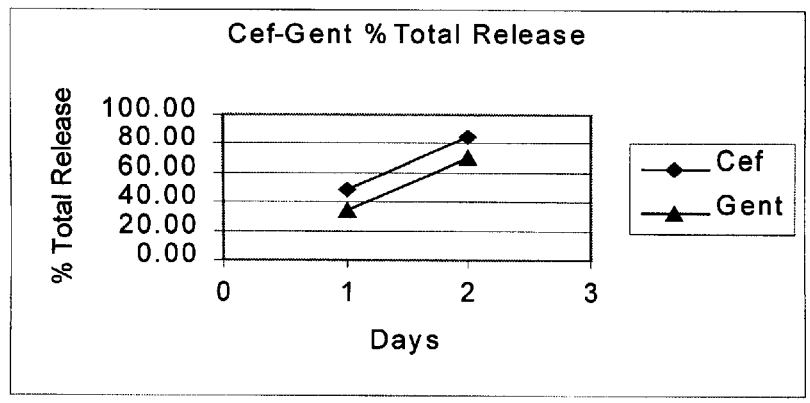
Figure 2:
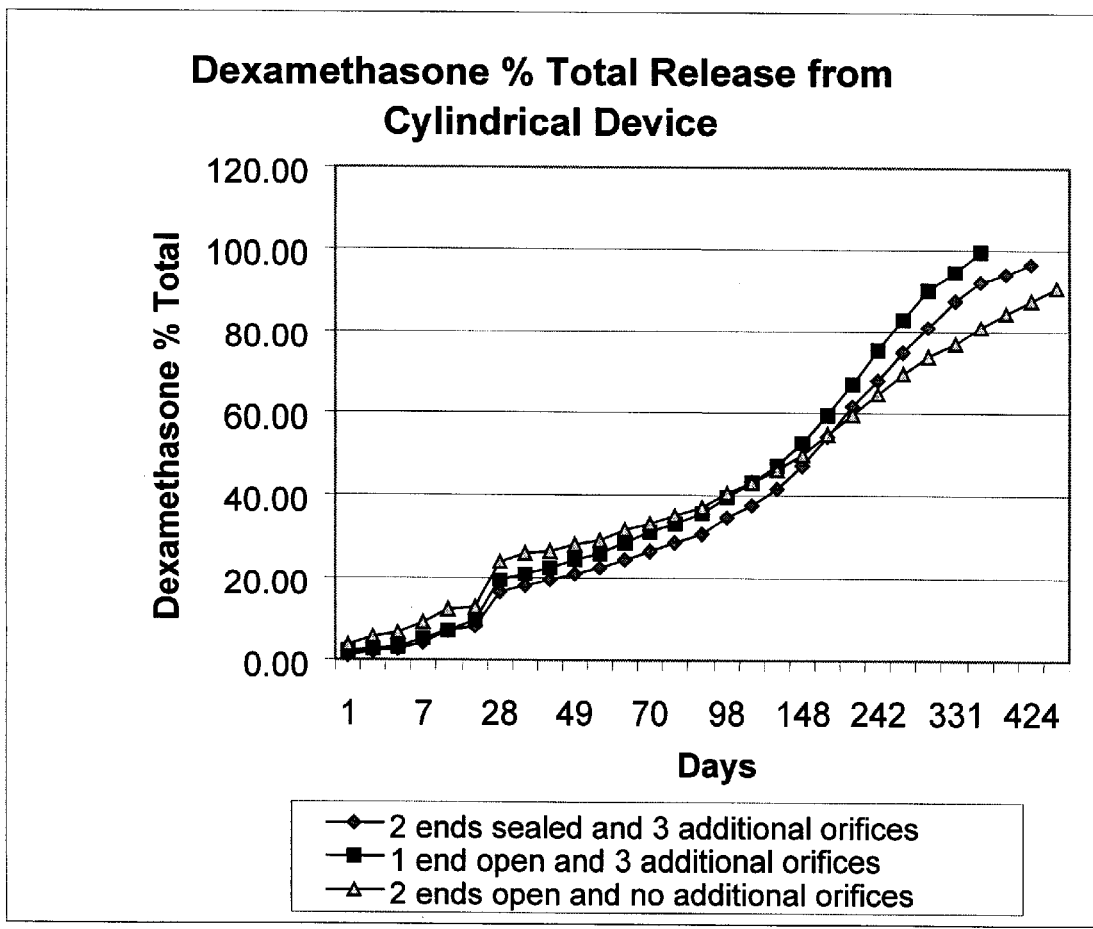
FIG. 2 is a graphical display of release data of dexamethasone from cylindrical devices made of poly(fluorinated ethylene propylene) (FEP), wherein the orifice configuration and number varied.
Figure 3:
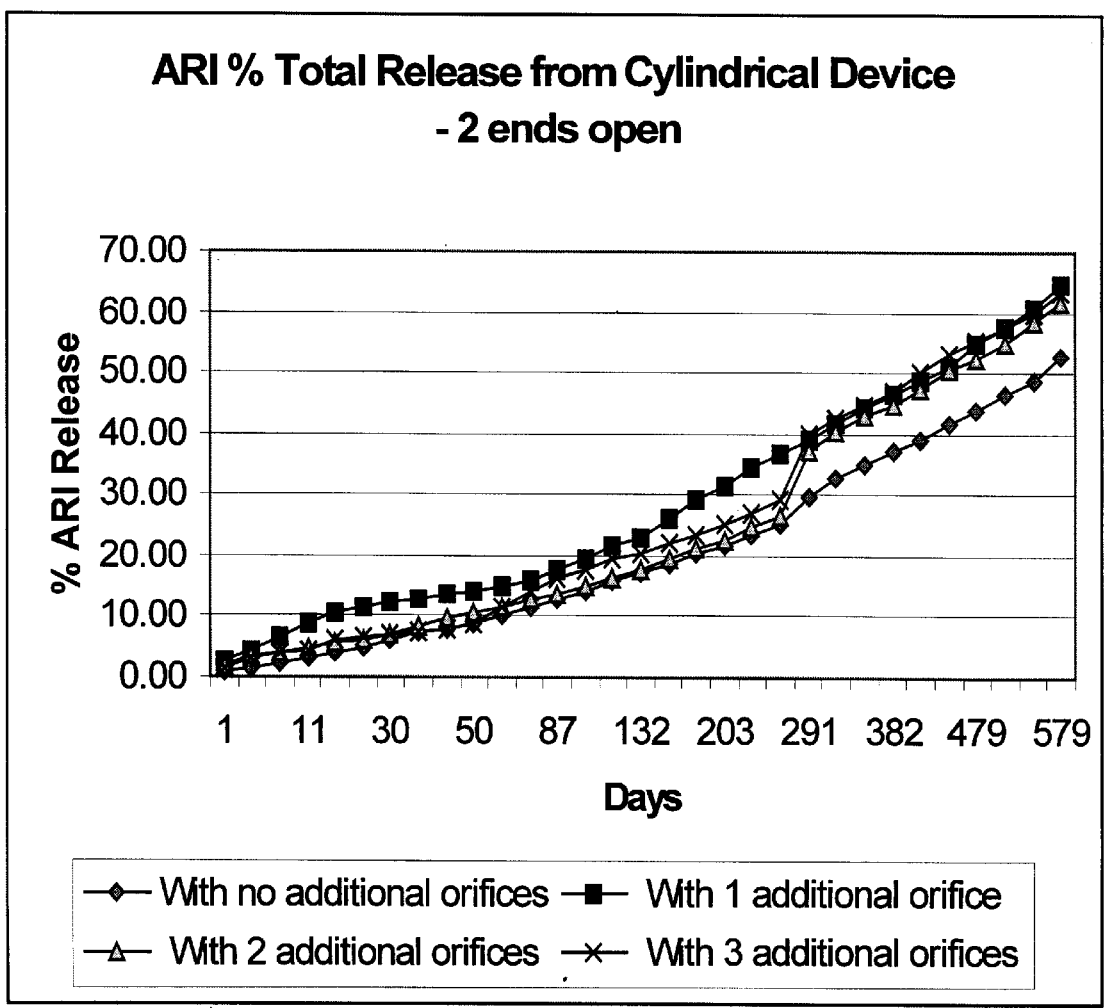
FIG. 3 is a graphical display of release data of an aldose reductase inhibitor (ARI) from cylindrical devices made from polytetrafluoroethylene. In this case, an orifice was created on each spherical face of the device by leaving the spherical faces open (ie., unsealed).
Figure 4:
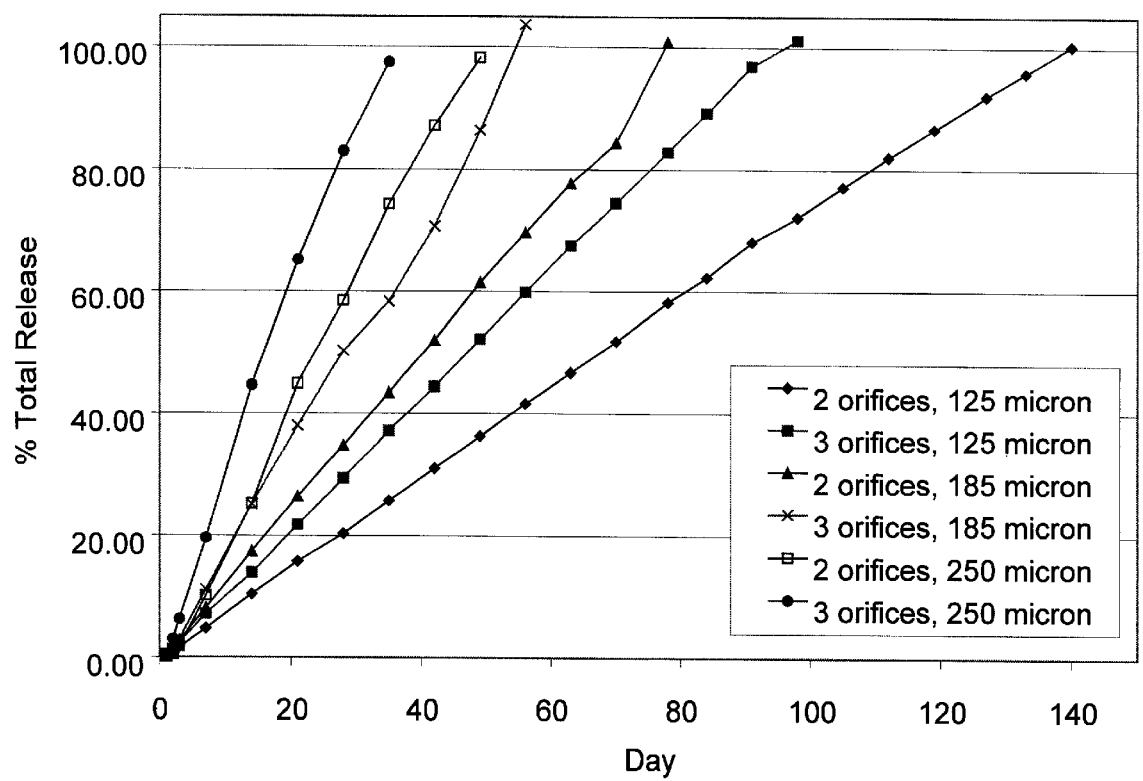
FIG. 4 is a graphical display of ganciclovir[9-[[2-hydroxy-1-(hydroxymethyl)ethoxy]-methyl]-guanine (DHPG)] release data from cylindrical devices made silicone, wherein each spherical face of the cylindrical device is sealed.

One of ordinary skill in the art would readily appreciate that the pharmaceutical devices and methods described herein can be prepared and practiced by applying known procedures in the pharmaceutical arts. Thus, the practice of the present invention employs, unless otherwise indicated, conventional techniques of pharmaceutical sciences including pharmaceutical dosage form design, drug development, pharmacology, of organic chemistry, and polymer sciences. See generally, for example, Remington: The Science and Practice of Pharmacy, 19th Ed., Mack Publishing Co., Easton, Pa. (1995) (hereinafter REMINGTON).

B. Definitions

As used herein, certain terms have the following defined meanings.

As used in the description and claims, the singular forms a, an and the include plural references unless the context clearly dictates otherwise. For example, the term a drug may refer to one or more drugs for use in the presently disclosed invention.

Controlled release refers to the release of a given drug from a device at a predetermined rate. Such rate of release can be zero order, pseudo-zero order, first order, pseudo-first order and the like. Thus, relatively constant or predictably varying amounts of the drug can be delivered over a specified period of time.

Delivery refers to the release of a drug from a device comprising that drug into an environment surrounding the device. The environment into which the drug so released may or may not be the ultimate site of activity for that drug. In some instances, the released drug may need to be transported to its ultimate site of activity.

Biocompatible means that the device, polymer or component is substantially non-immunogenic and leaves no toxic, potentially inflammatory or immunogenic reaction products at the tissue site of administration.

The term ocular refers to the eye, including all its muscles, nerves, blood vessels, tear ducts, membranes etc., as well as structures that are immediately connected with the eye and its physiological functions. The terms ocular, ocular structures and eye are used interchangeably throughout this disclosure.

Ocular delivery refers to delivery of a desired drug to the eye. Moreover, ocular delivery may include systemic delivery through the eye, because, as one of ordinary skill in the art recognizes, a localized delivery to a particular site in the eye may result, due to the highly perfused nature of the eye, in the drug being absorbed through the blood vessels and carried to a location remote from the eye leading to systemic delivery. Given this characteristic, it may be advantageous in some cases to aim for systemic delivery through the eye. Such systemic delivery is also within the scope of the present invention.

The term biodegradable means that the component, carrier or formulation degrades in biological media such as body fluids and anatomical structures comprising or bathed by body fluids. Alternatively, biodegradation refers to, in the context of a biodegradable polymer for example, the situation in which the molecular weight of the polymer decreases due to a reduction in the number of monomers with time. Examples of body fluids include blood, plasma, saliva, tears, lymph, urine, etc. Examples of anatomical structures comprising or bathed by body fluids include the oral cavity, the nasal cavity, the genitourinary tract, the respiratory tract, the gastrointestinal tract, ocular system, etc. Such erosion in body fluids may be due to factors such as dissolution, dispersion, friction, gravity, etc.

The term drug device or delivery device or simply device as used herein refers to a composition that contains and or delivers a drug to a subject and is generally considered to be otherwise pharmacologically inactive. The devices of this invention comprise an outer layer, a core and at least one orifice in the outer layer. The subject can be a human or any animal. The term animal includes any known animal as well as fishes, avians, and reptiles.

Outer layer is a layer of material that covers the entire core of a drug delivery device, except for the opening(s) provided in the outer layer by way of an orifice. Depending on the method of manufacture of the device, the outer layer and the drug core may or may not be substantially in contact with each other. The outer layer material can be made of a polymeric composition and, when in use, is substantially impermeable to body fluids and the drug to be delivered, wherein the influx of the body fluids and the efflux of the drug occurs substantially or entirely through the orifice(s).

Substantially impermeable, impermeable or non-permeable refer to the permeability characteristic of the outer layer of the device, wherein the influx and efflux of water or body fluids as well as the core composition including the drug across the outer layer of the device is de minimus, ie., nonsubstantial, except for that occurring through the orifices provided in the device. One of ordinary skill in the art may recognize that no device when implanted may remain completely impermeable to body fluids over extended periods of time. However, the objective of the present invention is achieved if the controlled delivery characteristics of the device are not substantially affected even if the device is shown to be or have been permeable to body fluids wherein such permeability occurs or has occurred through means other than the orifices provided in the device. For example, accidental puncturing of the device during implantation may make the device permeable. Where the device is of the refillable type, puncturing of the device may occur during such refillings. In these cases, the device may become permeable through such puncturing. However, the device should be considered impermeable or substantially impermeable so long as its controlled delivery characteristics are not affected.

Core comprises the drug to be delivered and, optionally, mixed with an adjuvant.

The term drug includes any known pharmacologically active agent as well as its pharmaceutically acceptable salt, prodrug such as an ester or an ether, or a salt of a prodrug, or a solvate such as ethanolate, or other derivative of such pharmacologically active drug. These salts, prodrugs, salts of prodrugs, solvates and derivatives are well-known in the art.

Salts of the pharmacologically active drugs may be derived from inorganic or organic acids and bases. Examples of inorganic acids include hydrochloric, hydrobromic, sulfuric, nitric, perchloric, and phosphoric acids. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of organic salts include: acetate, propionate, butyrate, hexanoate, heptanoate, undecanoate, palmoate, cyclopentanepropionate, adipate, alginate, aspartate, benzoate, citrate, oxalate, succinate, tartarate, lactate, maleate, filmarate, camphorate, nicotinate, pectinate, picrate, pivalate, tosylate, gluconate, digluconate, hemisulfate, methanesulfonate, ethanesulfonate, 2-hydroxyethanesulfonate, dodecylsulfate, camphorsulfonate, benzenesulfonate, 2-naphthalenesulfonate, thiocyanate, phosphate, glycerophosphate, and phenylpropionate. Several of the officially approved salts are listed in Remington, supra, Chapter 83.

The term derivative of a compound as used herein means a chemically modified compound wherein the chemical modification takes place at one or more functional groups of the compound and /or on an aromatic, alicyclic, or heterocyclic structures, when present. The derivative however is expected to retain the pharmacological activity of the compound from which it is derived.

The term prodrug refers to a precursor of a pharmacologically active compound wherein the precursor itself may or may not be pharmacologically active but, upon administration, will be converted, either metabolically or otherwise, into the pharmacologically active drug of interest. Several prodrugs have been prepared and disclosed for a variety of pharmaceuticals. See, for example, Bundgaard, H. and Moss, J., *J. Pharm. Sci.* 78: 122–126 (1989). Thus, one of ordinary skill in the art knows how to prepare these derivatives and prodrugs with commonly employed techniques of organic synthesis.

In addition, polymorphs, isomers (including stereoisomers, geometric isomer and optical isomers) and anomers of the pharmaceuticals described herein are contemplated.

Further, the term drug includes nucleic acid sequences. These nucleic acid sequences may be delivered as "naked" or as packaged in a vector, wherein the naked or the vector-packaged nucleic acid may provide the desired pharmacologic, physiologic or immunologic effect by interacting with the cellular membranes of the ocular tissue. On the other hand, the nucleic acid may be taken up by the ocular cells wherein the nucleic acid is incorporated into the cell and expressed to produce a protein. The protein thus produced may have a variety of physiologic, pharmacologic or immunologic functions. For example, in one aspect, the protein may act as an immunogen by binding to the ocular cells, thereby triggering an immunologic reaction that may result in an attack by killer T-cells to cause cell death. Such cell death is desirable when treating for example, cancerous conditions of the eye. In another aspect, the protein may stimulate growth of epithelial cells in an ocular tissue. Some growth factors deliverable by the devices of this invention include brain nerve growth factor (BNGF), celiary nerve growth factor (CNGF), vascular endothelial growth factor (VEGF). Several vectors, including viral (such as adenoviral) and non-viral (such as liposomal), as well as methods for incorporating nucleic acids in such vectors are known in the art.

The terms drug and pharmaceutical as used herein are identical in meaning and thus are used interchangeably.

An adjuvant is an agent that may affect any of (1) the rate of release of the drug; (2) the stability of the drug; (3) the solubility of the drug; or (4) physicochemical characteristics of the core itself, including compactness, pH, etc. However, an adjuvant does not include those ingredients that affect the release rate by providing an osmotic pressure or ion gradient. In one aspect, adjuvants may include solubilizing agents, solubility decreasing agents, and dispersing agents.

A solubilization agent increases the solubility of a pharmaceutical in the formulation. The solubilization agent preferably comprises between about 0.01% and about 20% by weight of the final formulation, and more preferably between about 0.1% and 10% by weight of the final formulation.

A solubility decreasing agent can be used in the formulation to achieve the desired release characteristics. Solubility of a drug can be decreased by techniques known in the art, such as by complexation, etc. Examples of complexation agents include: 2-hydroxynicotinic acid, 2-hydroxyphenylacetic acid, cyclodextrans, phthalic acid, polyethylene glycols, hydroquinone and derivatives thereof, caffeine, bile salts and acids.

As used herein, the term solubility refers to the extent to which a solute dissolves in a solvent, wherein the solute and "solvent" may be of the same or of different physical state. Thus, a solution of a solid or a liquid in any "solvent" such as a solid, liquid or gas is within the scope of this term.

Solubility can be expressed in many ways, such as: weight/volume (grams/mL); molality (number of moles of solute/1000 grams of solvent); mol fraction (fraction of the total number of mols present which are mole of one component); mol % (mol fraction×100); normality (number of gram equivalent weights of solute dissolved in 1000 mL of solution); % by weight (% w/w); % weight in volume (% w/v); % by volume (% v/v).

Solubility can also be described by terms such as: very soluble (less than 1 part of solvent per 1 part of solute); freely soluble (from 1 to 10 parts of solvent per 1 part of solute); soluble (from 10 to 30 parts of solvent per 1 part of solute); sparingly soluble (from 30 to 100 parts of solvent for 1 part of solute); slightly soluble (from 100 to 1000 parts of solvent for 1 part of solute); very slightly soluble (from 1000 to 10,000 parts of solvent for 1 part of solute); and practically insoluble, or insoluble (more than 10,000 parts of solvent for 1 part of solute). For further elaboration, see Remington, supra, Chapter 16, which is incorporated by reference.

A dispersing agent is an agent that facilitates the formation of a dispersion of one or more internal phases in a continuous phase. Examples of such dispersions include suspensions and emulsions, wherein the continuous phase may be water, for example, and the internal phase is a solid or a water-immiscible liquid, respectively. Thus, dispersing agents may include suspending agents and emulsifying agents.

Orifice refers to an opening in the outer layer through which, when the device is in use, body fluids can enter the device and the dissolved drug in the device can migrate out of the device. This expression is synonymous with "passageway" or "aperture" or "hole" or "bore" and the like. The orifices can have any shape, for example, spherical, cubical, ellipsoidal, cylindrical, conical, inverse-conical, irregular, and the like. The delivery device can have more than one orifice. When the device is fabricated with more than one orifice, the orifices can be construed as the functional equivalent of a single orifice.

The term area of the orifice refers to the area of a surface of a section of the outer layer that has been removed to provide the orifice. More specifically, it refers to either the outermost surface of the removed section of the outer layer (i.e., that surface of the outer layer that is farthest from the drug core) or the innermost surface of the removed section of the outer layer (i.e., that surface of the outer layer that is closest to the drug core), whichever has the smallest surface area. The surface area is measured as the area of the surface in a two-dimensional plane.

Thus, for example, when the orifice is cubical, the surface area of the orifice is the area represented by its two-dimensional plane, namely a square. When the orifice is cylindrical, the surface area of the orifice is the area of the circular plane, disregarding the height (ie., thickness of the outer layer). When the orifice is spherical, the surface area of the orifice is the area of the circular plane. When the orifice is conical, the surface area of the orifice is the area of that surface of the orifice that is closest to the drug core. When the orifice is inverse-conical shaped, the surface area of the orifice is the area of that surface of the orifice that is farthest from the drug core. When the orifice is formed by leaving unsealed an end of an open cylindrical tube, the area of the orifice refers to the area of a circle having the radius of the cylindrical device.

It is appreciated that, in some aspects, as for example when the device is cylindrical, a given surface of the removed section may have curvature. In calculating the area of that surface, the effects of curvature are ignored when, as described above, the surface is projected in a two-dimensional plane. As a practical matter, since the outer layer of the devices of this invention has, in general, a thickness of about 0.6 mm or less, the effect of this thickness (or height) has been ignored in calculating the area of the orifice. Thus, for example, in calculating the area of a cylindrical or spherical orifice, the only relevant measurement is the radius of the orifice.

The term total surface area of the device refers to the entire exterior surface area of the device without excluding the surface area of the orifice. For example, when the device is cylindrical, with one orifice on its longitudinal face, the total surface area of the device is calculated using the formula: $(p*2\pi r)+2\pi r^2$ wherein p and r are the length and radius of the device.

An effective amount is an amount sufficient to effect beneficial or desired results. An effective amount can be administered in one or more administrations, applications or dosages. Determination of an effective amount for a given administration is well within the ordinary skill in the pharmaceutical arts.

Administration refers to a method of placing a device to a desired site. The placing of a device can be by any pharmaceutically accepted means such as by swallowing, retaining it within the mouth until the drug has been dispensed, placing it within the buccal cavity, inserting, implanting, attaching, etc. These and other methods of administration are known in the art.

The term pharmaceutically acceptable is an adjective and means that the ingredient that is being qualified is compatible with the other ingredients of the formulation and not injurious to the patient. Several pharmaceutically acceptable ingredients are known in the art and official publications such as The United States Pharmacoepia describe the analytical criteria to assess the pharmaceutical acceptability of numerous ingredients of interest.

Concentrations, amounts, etc., of various components of this invention are often presented in a range format throughout this application. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 1% to 8% should be considered to have specifically disclosed subranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

C. The Devices

The present invention provides biocompatible controlled-release ocularly implantable drug delivery devices and methods for using such devices. The device comprises a drug core surrounded by a substantially impermeable polymeric outer layer which has one or more orifices through which body fluids may enter to dissolve the drug and through which the dissolved drug may efflux at a desired rate for a desired period. The present invention is particularly appropriate for drugs that are very active even in extremely small quantities and whose sustained long-term administration is sought.

The device can be implanted anywhere in a human or an animal to obtain localized or systemic effects of the drug that is released from the device. In some particular aspects, the device is implanted in the eye to treat or prevent a variety of conditions of the eye such as bacterial and viral infections, inflammation, cancerous growth, ocular pressure, haemorrhage, etc. In some aspects, the device can be made biodegradable after the release of the drug is completed.

The devices of the present invention may be of any preselected shape, such as spherical, cylindrical, cubical, conical, ellipsoidical, biconvex, hemispherical or near-hemispherical etc. By "near-hemispherical", it is meant that one face of the device is substantially flat, shallow convex or shallow concave, and the opposite face is deeply convex (i.e., the deeply convex face has a greater radius of curvature than the shallow convex, shallow concave, or substantially flat face).

The devices for ocular implantation are generally small such that the devices can be implanted in the fairly small ocular cavity. For example, when the device is cylindrical, it may be about 3–7 millimeters in height and about 0.5 to 4 millimeters in diameter. The volume of the device is such that the device holds sufficient amount of the drug to provide a continuous delivery over the implant's long delivery period, e.g., several weeks, months, or even longer, i.e., up to 2 or more years. The volume needed thus depends on characteristics such as drug solubility, drug delivery rate, period of delivery, drug's half life, etc. Once implanted, the device gives a continuous delivery of the drug to internal regions of the eye without requiring additional invasive penetrations into these regions.

The following description provides greater details of the various aspects of the devices and the methods.

1. The Polymeric Outer Layer

Various biocompatible substantially impermeable polymeric compositions may be employed in preparing the outer layer of the devices. Some relevant factors to be considered in choosing a polymeric composition include: compatibility of the polymer with the biological environment of the implant, compatibility of the drug with the polymer, ease of manufacture, a half-life in the physiological environment of at least several days, no significant enhancement of the viscosity of the vitreous, and the desired rate of release of the drug. Depending on the relative importance of these characteristics, the compositions can be varied. Several such polymers and their methods of preparation are well-known in the art. See, for example, U.S. Pat. Nos. 4,304,765; 4,668,506 4,959,217; 4,144,317, and 5,824,074, Encyclopedia of Polymer Science and Technology, Vol. 3, published by Interscience Publishers, Inc., New York, latest edition, and Handbook of Common Polymers by Scott, J. R. and Roff, W. J., published by CRC Press, Cleveland, Ohio, latest edition.

The polymers of interest may be homopolymers, copolymers, straight, branched-chain, or cross-linked derivatives. Some exemplary polymers include: polycarbamates or polyureas, cross-linked poly(vinyl acetate) and the like, ethylene-vinyl ester copolymers having an ester content of 4 to 80% such as ethylene-vinyl acetate (EVA)

copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3–3-dimethyl butanoate copolymer, and ethylene-vinyl benzoate copolymer, or a mixture thereof.

Additional examples include polymers such as: poly(methylmethacrylate), poly(butylnethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), chlorinated poly(ethylene), poly(trifluorochloroethylene), poly(ethylene chlorotrifluoroethylene), poly(tetrafluoroethylene), poly(ethylene tetrafluoroethylene), poly(4,4'-isopropylidene diphenylene carbonate), polyurethane, poly(perfluoroalkoxy), poly(vinylidenefluoride), vinylidene chloride-acrylonitrile copolymer, vinyl chloride-diethyl fumarate copolymer, silicone, silicone rubbers (of medical grade such as Silastic® Medical Grade ETR Elastomer Q7–4750 or Dow Corning® MDX 4-4210 Medical Grade Elastomer); and cross-linked copolymers of polydimethylsilane silicone polymers.

Some further examples of polymers include: poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls) such as polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, poly(acrylate), poly(methacrylate), poly(oxides), poly(esters), poly(amides), and poly(carbonates), or a mixture thereof.

In some aspects, the devices may be biodegradable wherein the outer layer degrades after the drug has been released for the desired duration. The biodegradable polymeric compositions may comprise organic esters or ethers, which when degraded result in physiologically acceptable degradation products, including the monomers. Anhydrides, amides, orthoesters or the like, by themselves or in combination with other monomers, may find use. The polymers may be addition or condensation polymers, cross-linked or non-cross-linked. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. In some aspects, the polymer is polytetrafluoroethylene, (commercially known as Teflon®), ethyl vinyl alcohol or ethylene vinyl acetate.

Some examples of biodegradable polymers useful in the present invention include: hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-ε-caprolactone, polydimethylsiloxane, polyamides, polyvinylpyrollidone, polyvinylalcohol phthallate, waxes such as paraffin wax and white beeswax, natural oils, shellac, zein, or a mixture thereof.

Suitable biodegradable polymeric compositions can be easily obtained since the decomposition rate of biodegradable polymers can be varied by chemical modification and/or by varying the component ratios and/or by varying the molecular weight. In case of certain polymers, isomerism can give rise to polymers with distinct characteristics. For example, by using the L-lactate, a slowly eroding polymer is achieved, while erosion is substantially enhanced with the lactate racemate.

2. The Core

The core of the delivery device comprises the drug to be delivered and may optionally comprise a pharmaceutically acceptable adjuvant. There is no critical upper or lower limit as to the amount of drug that can be incorporated into the core of the device. Thus, the ratio of drug to device is dictated by the desired time span, the release rate, and the efficacy of the drug. For example, the drug may be from about 1 to 80, and in some aspects, from about 20 to 40 weight percent of the device. Generally, devices of various sizes can be prepared to house from 0.05 ng to 50 grams of drug or more, with individual devices containing, for example, 25 ng, about 1 µg, about 10 µg, about 100 µg, about 1 mg, about 5 mg, about 250 mg, about 500 mg, about 1.5 g, or the like.

The drug can be deposited in the device as a dry powder, particles, granules, or as a compressed solid. The drug may also be present as a solution or be dispersed in a polymer matrix. The polymers used in the matrix with the drug are bio-compatible with body tissues and body fluids and can be biodegradable or substantially insoluble in the body fluids. Any of the above-described biocompatible polymer compositions can be used to prepare the matrix. The amount of polymer in the core may be from about 0% to 80 wt % by weight. These polymers are commercially available and methods for preparing polymer matrices are well-known in the art. See, for example, U.S. Pat. No. 5,882,682.

a) Drugs

A wide variety of systemic and ocular conditions such as inflammation, infection, cancerous growth, may be prevented or treated using the drug delivery devices of the present invention. More specifically, ocular conditions such as glaucoma, proliferative vitreoretinopathy, diabetic retinopathy, uveitis, keratitis, cytomegalovirus retinitis, herpes simplex viral and adenoviral infections can be treated or prevented.

The following classes of drugs could be delivered using the devices of the present invention: anesthetics, analgesics, cell transport/mobility impending agents such as colchicine, vincristine, cytochalasin B and related compounds; antiglaucoma drugs including beta-blockers such as timolol, betaxolol, atenolol, etc; carbonic anhydrase inhibitors such as acetazolamide, methazolamide, dichlorphenamide, diamox; and neuroprotectants such as nimodipine and related compounds.

Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericine B, ketoconazole, and related compounds; anti-viral agents such as trifluorothymidine, acyclovir, ganciclovir, DDI, AZT, foscamet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators. Anticlotting agents such as heparin, antifibrinogen, fibrinolysin, anti clotting activase, etc., can also be delivered.

Antidiabetic agents that may be delivered using the present devices include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, nucleic acids, saccharides, lipids, glycolipids, glycoproteins, and other macromolecules can be delivered using the present devices. Examples include: endocrine hormones such as pituitary, insulin, insulin-related growth factor, thyroid, growth hormones; heat shock proteins; immunological response modifiers such as muramyl dipeptide, cyclosporins, interferons (including α, β, and γ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta$_2$, erythropoetin; anti-neogenesis proteins (e.g., anit VEGF, Interfurons), among others and anticlotting agents including anticlotting activase. Further examples of macromolecules that can be delivered include monoclonal antibodies, brain nerve growth factor (BNGF), celiary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nulceic acids can also be delivered wherein the nucleic acid may be expressed to produce a protein that may have a variety of pharmacological, physiological or immunological activities. Thus, the above list of drugs is not meant to be exhaustive. Practically any drug may be used in the instant invention, and there are no particular restrictions in terms of molecular weight and so forth.

Additional examples of beneficial drugs that may be employed in the present invention and the specific conditions to be treated or prevented are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J.

b) Adjuvants

In certain aspects, it may be advantageous to include one or more adjuvants in the core to alter the release characteristics of the drug from the device, or to enhance the stability of the drug or to alter the solubility of the drug in body fluids or to alter the physicochemical characteristics of the core itself. Adjuvants may include swelling agents to improve the accessibility of the drug to body fluids or, alternatively, adjuvants may be used to slow the release of drug from the device. Examples of such solubility decreasing agents include complexation agents, hydrophobic materials and insoluble polymers. A surfactant or an effervescent base may be helpful in certain cases to overcome surface tension effects, etc.

Adjuvants may also include diluents, buffering agents and preservatives. Examples of buffering agents include alkali or alkaline earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8, during manufacturing, storage and delivery conditions. Examples of preservatives include benzalkonium chloride, antioxidants, such as ascorbic acid, sodium bisulfite, parabens, benzyl alcohol. These agents may be added in amounts of from about 0.001 to about 5%.

Where the implant is positioned such that no portion of the implant is in direct contact with the site of action, for example, the vitreous, diffusion of the drug through biological membranes to the site of action may be facilitated by permeation enhancers (e.g., DMSO, detergents, ethanol, isopropyl myristate, oleic acid, azome and the like). The determination of proper amounts and methods for using permeation enhancers are within the ordinary skill in the art. See, for example, Remington, supra, Chapter 41.

3. The Orifice

When in use, the devices of this invention are substantially impermeable to both the body fluids of the environment and to the drug, except through the orifices provided in their outer layer. Thus, the influx of body fluids and the efflux of drug solution occurs primarily, if not entirely, through the orifice. The desired rate of release of the drug is achieved by providing an orifice of proper area relative to the area of the device and taking into account parameters such as the solubility properties of the drug and the optionally present adjuvants. It is preferred that the orifice extend through the entire thickness of the outer layer such that there is immediate exposure of the core to the body fluids when the device is implanted.

The number, configuration, shape and size of the orifices are chosen to provide the release rate required to suit a treatment regimen. In some aspects, more than one orifice may be provided in the device for the release of drug. When more than one orifice is provided, the plurality of orifices should be construed to be of functionally equivalent to a single orifice. The orifices can be positioned anywhere on the device including the edges, on the same face of the device, or on different faces. The number of orifices in each device may range from about 1 to about 5 or more.

The orifices are generally spherical but may be of any design, such as cubical, pyramidical, ellipsoidical, conical, and the like, so long as the desired release rate is achieved.

When the orifice is spherical, its diameter may range from about 0.005 mm or less to about 6 mm. In some aspects, the diameters may range from about 0.001 mm to 0.5 mm.

The orifice has an area which corresponds to less than 10 percent of the area of the device. In some aspects, the orifice has an area which is about less than 7 percent of the area of the device. In some aspects, the orifice has an area which is about less than 2 percent, or less than 1 percent of the area of the device. When the device is provided with a number of orifices, the sum of the areas of all the orifices comprises less than 10 percent of the area of the device.

As provided in the Definitions section, the term "orifice" is a broad term which represents an aperture, hole, or opening. Thus, when the device is cylindrical, an orifice can also be formed by leaving one of the two spherical faces open, i.e., unsealed. In some aspects, both the spherical faces of a cylindrical device can be left open, forming an orifice at each spherical face. It is appreciated that to form an orifice by this manner, the spherical faces need not be completely left open, i.e., partial opening may also lead to an orifice at either end of the cylindrical device. In addition, the cylindrical device may also be equipped with additional orifices on other surfaces.

4. Additional Aspects

In some aspects, it may be desirable for the device to further comprise a backing layer. The backing layer will be in contact with the surfaces of the device which are not in contact with or adjacent the desired site of therapy. The composition of the backing layer may vary with the drug employed, the site of implantation, compatibility with agents in addition to the drug which may be employed in the device and the like. The backing layer is biocompatible and substantially impermeable to the drug contained within the device. Exemplary compositions for the backing layer include polyesters (e.g., mylar), polyethylene, polypropylene, polyethylene vinyl acetate, polytetrafluoroethylene, aclar, silicone, silastic, nylon, and other film material which are well known and/or commercially available.

The device may also comprise an adhesive layer or coating for securing the device at the desired insertion site, particularly where the device is to be placed substantially on the outer surface of the eye over an avascular region. The adhesive layer may be in the form of a release liner or peel strip. The adhesive layer may be made of any suitable material which is biocompatible. Many such adhesive layer-forming polymers are known in the art. See, for example, U.S. Pat. Nos. 5,693,335 and 5,006,342.

In some aspects, the device can be operated as a refillable device. For example, where the molecular weight of the drug, the desired dosage, the period of administration (as in chronic therapy) and the like are such that the size of the device required to contain the desired amount of drug is incompatible with the area of implantation, a device comprising a refillable reservoir may be used. The device may be refilled with any one or all of the components present in the original core. The device may be refilled by, for example, injection of the core material directly into the reservoir of the device, taking particular care not to compromise the ability of the device to release the drug at the desired rate. Thus, in some aspects, the outer surface of the device may comprise a self-sealing layer made of a non-biodegradable material and is capable of resealing. See, for example, U.S. Pat. No. 4,300,557, for a description of refillable type devices.

While the present invention focuses on ocular implantation of the devices disclosed herein, the devices can be easily implanted in other areas of the body. Thus, the devices of the present invention may be adapted for gastrointestinal, buccal, cervical, rectal, vaginal, intrauterine, nasal, and dermal implant use and the like. In addition, one or more of the devices may be administered at one time and more than one agent may be included in the core.

D. Implantation

Methods of implanting a drug delivery device are well-known in the art, and include surgical means, injection, trocar, etc. The ocular implant devices of the present invention may be implanted at several anatomical regions of the eye. For example, the devices may be placed substantially upon the outer surface of the eye and may be anchored in the conjunctiva or sclera, or episclerally or intrasclerally over an avascular region. The devices may also be implanted substantially within the suprachoroidal space over an avascular region such as the pars plana or a surgically-induced avascular region.

Alternatively, the devices may be implanted in an area in direct communication with the vitreal chamber or vitreous so as to avoid diffusion of the drug into the bloodstream. The devices can also be implanted in the anterior chamber. On the other hand, diffusion of the drug to the desired site may be facilitated by forming holes or tunnels through the layers of the sclera or other tissue which communicate, with the desired site of therapy which lie beneath the device. As a result, the tunnels will lie beneath the implant and serve to substantially direct the flow of the drug from the device to the desired site of therapy. These holes may be formed by surgical procedures which are known in the art or through the application of a permeability enhancing agent described above such as ethanol, oleic acid, isopropyl myristate and the like.

Alternatively, the device may be inserted so as to directly communicate with the vitreal chamber. A hole of suitable size may be made through the sclera to communicate with the base of the vitreous body through the pars plana. The implant is positioned over the hole within the scleral bed and the flap of the trap door is sewn back into place. Such placement of the implant will allow for the ready diffusion of the drug into the vitreous and into the intraocular structure.

The devices can be implanted by using an implanter, the operation of which is described in U.S. Pat. Nos. 3,921,632 and 4,451,254. Surgical procedures, such as those known in the art, may be necessary to position large implants. For example, the implants can be inserted through a sclerotomy into the suprachoroid. In this instance, the sclera is cut to expose the suprachoroid. An implant is then inserted on either side of the incision. Alternatively, a partial-thickness scleral trapdoor can be fashioned over the suprachoroid or an avascular region. An implant is then inserted and the scleral flap is sewn back into place to secure the implant.

In many aspects, the device per se can be implanted. In some aspects, the device can be placed in a "container" which is then implanted. For example, the device can be placed in a "container" such as an artifical lens or a limb first and the artificial lens or limb is then ocularly implanted, for example in the anterior chamber. Thus, the devices of this invention are introduced into a body cavity or area in many different ways.

E. Methods of Making Implants

Several techniques such as solvent evaporation methods, phase separation methods, interfacial methods, extrusion methods, molding methods, injection molding methods, heat press methods and the like can be used to prepare the outer layer and or the entire device. Such techniques are well-known in the art. See, for example, U.S. Pat. Nos. 5,164,188 and 5,660,847, and Handbook of Common Polymers, by J. R. Scott and W. J. Roff, Section 64, (1971) published by CRC Press, Cleveland, Ohio.

In one particular aspect, a technique known as injection molding is used. For a general description of this technique, see for example, U.S. Pat. Nos. 3,432,592, 4,801,460, 4,806, 337, 5,004,601, and 5,082,655, and Cuff, G. and Raouf, F., Pharmaceutical Technology, 96–106 (1998), which are incorporated by reference.

Briefly, the injection molding technique comprises several steps. In the first step, the mold is closed and clamped to prevent it from opening. In the second step, the polymeric material is injected through a nozzle and into the cavities of the mold by moving a screw to a predetermined distance. By adjusting the distance the screw must be moved, the amount of material that is injected into the mold is controlled. The screw may be displaced further to facilitate packing of additional material into mold cavities to fill the voids that may have been generated when the mold cools after the first injection. The various parameters of the injection and packing steps, such as packing time, packing pressure, injection rate, injection pressure can be automated. The mold is cooled and the screw is returned to its pre-injection position. The mold is opened and the molded parts (in this case, the implants) are ejected. See Cuff and Raouf, supra.

1. Methods of Forming the Outer Layer

The biocompatible, substantially impermeable outer layer can be obtained by coating the core with a polymeric composition described above. The coat can be applied using organic solvents, and the solvents are vacuum stripped from the coat to leave a dry coat. The polymer, at a concentration of from about 10 to about 80 weight percent is dissolved or suspended in an organic solvent at the appropriate temperature, for example for polylactic polymer, between 60° to 90° C. The resulting mixture can be cut, molded, injection molded, extruded, or poured or sprayed onto a pre-formed core into any shape or size for implantation. The spraying can be accomplished in a rotating pan coater or in a fluidized bed coater until the desired coating thickness is achieved.

Alternatively, the core may be dip coated or melt coated. This type of coating is especially usefull with waxes and oils. In another embodiment, the core may be compression coated, wherein a suitable polymeric composition may be pressed onto a preformed core. In another aspect, an adhesive coat such as shellac or polyvinyl acetate phthallate (PVAP) is applied to the core prior to applying the impermeable coating in order to improve adhesion of the impermeable coating to the core. These techniques are well-known in the art. See, for example, Handbook of Common Polymers, by J. R. Scott and W. J. Roff, Section 64, (1971) published by CRC Press, Cleveland, Ohio.

When the outer layer is injection molded or extruded into the desired shape, the cavity formed by the outer layer can be then filled with the drug composition. Then, the ends are sealed with an end cap. At least one orifice is drilled in the lead end of the device. Optionally, an orifice is drilled, or preformed in the wall, or an orifice is sealed with a break-off tab that is broken open, or cut open, or the like, at the time of use.

Alternatively, the core-free device may be loaded with drug by, for example, immersing the device in a solution comprising the drug for a time sufficient for absorption of the drug. The device may be equipped with a hollow fiber and the drug may be directly loaded into the fiber and the device subsequently sealed. Where the activity of the drug will not be compromised, the drug-filled device may then be dried or partially dried for storage until use. This method may find particular application where the activity of the drug of choice is sensitive to exposure to solvents, heat or other aspects of the conventional solvent-evaporation, molding, extrusion or other methods described above.

Where a backing layer is to be employed, the polymer solution may be layered directly onto the backing layer material and the solvent evaporated or a release liner attached to the underlying structure. Where desired, a release liner may then be placed on top of the polymer layer. Where the device is to comprise an adhesive layer, the adhesive layer may be applied to the release liner prior to placing the release liner on the polymer layer and/or membrane layer. When the release liner is later removed prior to insertion of the device, the adhesive layer will substantially remain on the polymer layer.

Where a refillable reservoir device is desired, the device may be molded in two separate portions. At least one of these separate portions may be substantially concave. The two portions, which comprise the body of the device, may then be sealed together with a biocompatible adhesive, such as a silicone adhesive, to form a device having a substantially hollow center which may serve as a reservoir or depot for the drug. Alternatively, devices comprising a reservoir may be produced by conventional form-fill-seal techniques. The refillable device may also be manufactured employing injection molding techniques wherein the refillable device may be filled with the drug or drug suspension after the outer layer is formed. Alternatively, the device may be co-molded so that the outer surface and the drug core are formed substantially simultaneously by, for example, co-injection into a mold during injection molding.

The thickness of the outer layer should be selected as a function of the material properties and the desired release rate. The outer layer thickness is not critical as long as the specified functions of the outer layer are fulfilled. The outer layer thickness may be, for example, from about 0.05 mm to 3 mm. The thickness of the coating necessary to provide results in accordance with the present invention can be determined by using techniques that are well-known in the art. See, for example, Handbook of Common Polymers, supra. Devices can be prepared with differing coating thicknesses but without an orifice, and dissolution tests on these devices can be performed. The desired coating thickness can be selected by optimizing the conditions under which the drug is not released from the device during the desired duration of controlled release.

2. Making the Core

The core of the device of the present invention may be prepared using conventional tablet excipients and formulation methods and compressed into its final stage using standard tablet compressing machines. Depending upon the solubility and the amount of drug to be included in the core, any generally accepted soluble or insoluble inert pharmaceutical filler (diluent) material may be used to bulk up the core or to solubilize the drug. These materials include but are not limited to sucrose, dextrose, lactose, fructose, xylitol, mannitol, sorbitol, glycerol monostearate, dicalcium phosphate, calcium sulfate, calcium carbonate, starches, cellulose, polyethylene glycols, polyvinylpyrrolidones, polyvinyl alcohols, sodium or potassium carboxmethylcelluloses, gelatins, or mixtures of thereof.

In addition, the drug may be compressed with a small amount of lubricant. It is preferred that a lubricant be mixed with the drug and excipients prior to compression into a solid core. Any generally accepted pharmaceutical lubricant, including calcium or magnesium soaps may be used. Most preferred is magnesium stearate in an amount of about 0.25–5 percent by weight of the core.

Drugs may also be formulated with a small amount of a binder material such as gelatin or polyvinylpyrrolidone (i.e., 94–99.75% of the core comprises the drug). In such cases, the components of the core may be subjected to wet granulation.

The particular excipient chosen is dependent in part upon the solubility of the drug in the bodily fluid. The ratio of drug to excipient is based in part upon relative solubility of the drug in the bodily fluid and the desired rate of release. If the drug is relatively soluble, it may be desirable to slow down the erosion of the core by using a relatively insoluble excipient such as dicalcium phosphate.

The complete mixture of drug, lubricant, excipient, etc., in an amount sufficient to make a uniform batch of cores may be directly used or can be compressed in a conventional production scale tableting machine at normal compression pressures, i.e., about 2000–16000 lbs/sq. in.

3. Making the Orifice

The orifice may be formed using any technique known in the art. For instance, the orifice may be made using a needle or other form of boring instrument such as a mechanical drill or a laser to remove a section of the impermeable portion of the device. Alternatively, a specially designed punch tip may be incorporated into the compressing equipment, in order to pierce through the impermeable portion at the point of compaction.

The orifice may be made by drilling the appropriate size hole through a wall of the device using a mechanical or laser-based process. In the preferred embodiment, a digital laser marking system is used to drill the holes required. This system allows for an array of apertures to be drilled on both faces of a dosage form simultaneously and at rates suitable for production of dosage forms.

The process utilizes a digital laser marking system (for example the DigiMark™ variable marking system, available from Directed Energy, Inc.) to produce an unlimited number of holes through the surface or coating of the dosage form, at rates practically suitable for production of dosage forms.

The steps involved in this laser drilling process are as follows: a digital laser marking system is focused at a laser stage; the dosage form is moved onto the laser stage of the digital laser marking system is pulsed to energize those laser tubes needed to drill the desired apertures along a linear array on the dosage form, the dosage form is moved forward on the laser stage and the digital laser marking system is again pulsed as needed to produce an additional linear array of apertures; the dosage form is then removed from the laser stage.

Orifices and equipment for forming orifices are disclosed in U.S. Pat. Nos. 3,845,770; 3,916,899; 4,063,064 and 4,008,864. Orifices formed by leaching are disclosed in U.S. Pat. Nos. 4,200,098 and 4,285,987. Laser drilling machines equipped with photo wave length detecting systems for orienting a device are described in U.S. Pat. No. 4,063,064 and in U.S. Pat. No. 4,088,864.

F. Methods for Testing the Device

In order to define the potential drug-release behavior of the devices in vivo, the device may be maintained in a measured volume of a saline solution. The mixture is maintained at 37° C. and agitated or stirred slowly. The appearance of the dissolved drug as a function of time may be followed spectrophotometrically or by other analytical means. While release may not always be uniform, normally the release will be free of substantial fluctuations from some average value which allows for a relatively uniform release, usually following a brief initial phase of rapid release of the drug. Additional methods are known in the art. See, for example, Remington, supra, Chapter 94.

G. Specific Examples

Ocular devices comprising various types of drugs were prepared and tested for their controlled release properties and the duration of release was measured. Cylindrical devices from polytetrafluoroethylene, polyfluorinated ethylenepropylene (FEP) or silicone materials were prepared with varying number and configuration of orifices. These characteristics were summarized in Table 1. The release data were summarized in Table 2 and graphically displayed in FIGS. 1A–1F and 2–4.

In addition to varying the materials used for making the device, the number and configuration of orifices, as well as the drug to be delivered were varied. Gentamicin is an example of very soluble low molecular weight drug. Dexamethasone and cefazolin are examples of practically insoluble drugs of low molecular weight. DHPG or ganciclovir[(9-[[2-hydroxy-1-(hydroxymethyl)ethoxy]-methyl]-guanine)] is a freely soluble drug of low molecular weight whereas BSA (bovine serum albumin) is an example of a freely soluble macromolecule.

As more fully discussed in the Examples below, the data indicate that the present devices having the orifice area/total surface area of less than 10% can be successfully used to deliver a variety of drugs in a controlled manner for a duration of several weeks or even months. These characteristics are maintained regardless of the number and configuration of orifices present in the device. Moreover, unlike the prior art devices, the present devices do not require the presence of an osmotic agent, or an ion to propel the drug from the device.

While the above described embodiments of the invention are described in terms of preferred ranges of the amount of effective agent, these preferences are by no means meant to limit the invention. As would be readily understood by one skilled in the art, the preferred amounts, materials and dimensions, actual release rates and duration of release depend on a variety of factors in addition to the above, such as the disease state being treated, the age and condition of the patient, the route of administration, as well as other factors. Thus, the following examples should be viewed as mere illustrations and not limitations on the scope of the invention disclosed herein.

EXAMPLES

Examples 1–6

Cylindrical Devices with Varied Number and Configuration of Orifices

A Teflon® tube obtained from Small Parts, Inc., Florida of 0.97 mm internal diameter and 1.31 mm outer diameter was used to prepare the cylindrical devices of Examples 1–6. In all these Examples, the orifice(s) in each device is spherical. In the case of Examples 1–3 and 5, each orifice had an internal diameter of 0.25 mm. The orifice of the device in Example 6 had an internal diameter of 0.3 mm. The orifice of the device in Example 4 was formed by leaving open (unsealed) one spherical face of the cylindrical device. The length of the device varied in each case, and ranged from 3.7 mm (for Example 6) to 7.2 mm (for Examples 2 and 4). These characteristics were summarized in Table 1.

TABLE 1

| | Drug | # orifices | Total orifice surface area mm$^2$ | Surface area of the device mm$^2$ | % orifice area/device surface area | Wt. of Drug mg | # days of release |
|---|---|---|---|---|---|---|---|
| 1 | Fluorescein | 1 | 0.049 | 24.10 | 0.204 | 4.1 | 8 |
| 2 | BSA | 1 | 0.049 | 32.33 | 0.152 | 3.5 | 21 |
| 3 | Gentamicin | 1 | 0.049 | 26.15 | 0.188 | 3.3 | 61 |
| 4 | Gentamicin | 1 | 0.739 | 32.33 | 2.286 | 3.9 | 0.75 |
| 5 | Cefazolin acid | 3 | 0.147 | 30.27 | 0.487 | 3.9 | 81 |
| 6 | Gentamycin + Cefazolin acid | 1 | 0.071 | 17.92 | 0.394 | 0.376 | 2 |
| 7 | Dex | 3 | 0.589 | 31.26 | 1.884 | 2.9 | 424 |
| 8 | Dex | 4 | 1.283 | 31.26 | 4.104 | 3.4 | 365 |
| 9 | Dex | 2 | 1.388 | 23.28 | 5.962 | 2.6 | 455 |
| 10 | ARI | 3 | 1.674 | 24.10 | 6.948 | 2 | 579 |
| 11 | ARI | 4 | 1.871 | 28.21 | 6.631 | 2.6 | 579 |
| 12 | ARI | 5 | 2.067 | 28.21 | 7.327 | 2.6 | 579 |
| 13 | ARI | 2 | 1.478 | 24.10 | 6.134 | 2.2 | 579 |
| 14 | DHPG | 2 | 0.025 | 56.11 | 0.044 | 5 | 140 |
| 15 | DHPG | 3 | 0.037 | 56.11 | 0.066 | 5 | 91 |
| 16 | DHPG | 2 | 0.054 | 56.11 | 0.096 | 5 | 78 |
| 17 | DHPG | 3 | 0.081 | 56.11 | 0.144 | 5 | 56 |
| 18 | DHPG | 2 | 0.098 | 56.11 | 0.175 | 5 | 56 |
| 19 | DHPG | 3 | 0.147 | 56.11 | 0.262 | 5 | 42 |
| 20 | DHPG | 2 | 15.835 | 196.35 | 8.065 | 50 | 24 | r = ID/2
Open end area = 3.1416 × r$^2$
r$_{id}$ = ID/2
Orifice area = 3.1416 × r$_{id}^2$
Tube OD = 2 × r$_{od}$
Surface area = 3.1416 × OD × length + 2 × 3.1416 r$_{od}^2$ In each case, the general procedure for preparing the cylindrical device was as follows. The desired number of orifices on the longitudinal surface (except in the case of Example 4) of the Teflon® tube were provided by using a mechanical drill. Where there were multiple number of orifices, the orifices were spaced approximately 1–2 mm from each other. The Teflon® tube was cut using a sharp knife, and sealed with epoxy resin on one end, about 3–4 mm from the nearest orifice (except in the case of Example 4). The tube was weighed on a microbalance. The drug to be delivered was packed into the tube using a spatula and a small metal plunger. When the desired amount of the drug was packed, the tube was cut on the open-end at a distance of about 0.1–0.2 mm from the packed drug. The open end of the tube was sealed. The total orifice area/total surface area of the device ranged from 0.152% (Example 2) to 2.286% (Example 4).

In the case of Example 1, the device was 5.2 mm long and comprised 4.1 mg of fluorescein sodium, obtained from EM Science, NJ. The device in Example 2 was 7.2 mm long and comprised 3.5 mg of BSA, obtained from Sigma Chemical Co., Milwaukee, Wis. The device in Example 3 was 5.7 mm long and comprised 3.3 mg of gentamicin. The device in Example 4 was 7.2 mm long and comprised 3.9 mg of gentamicin. The device in Example 4 was distinct from the devices of Examples 1–3 in that in the latter case, each of the devices contained one orifice on its longitudinal surface, whereas, in Example 4, the orifice was formed by leaving open (i.e., left unsealed) one spherical face.

The device in Example 5 was 6.7 mm long and comprised 3.9 mg of cefazolin. Cefazolin sodium powder was obtained from LyphoMed, Inc., and the cefazolin acid was precipitated by using an acid. The term cefazolin as used throughout this application refers to the cefazolin acid prepared in this manner. The device in Example 6 was 3.7 mm long and comprised a combination of gentamicin and cefazolin in a mixture that ranged from 1:3 to 3:1, with the total weight being 0.376 mg.

Release Study

In each case, the delivery device was placed in 4–10 ml of saline solution in a vial. The vial was incubated at 37° C. Saline samples of approximately 1–5 ml were taken at specified times while adding to the vial an equal amount of fresh saline. The amount of fluorescein released was measured using standard analytical procedures that are well-known for the assay of the drug in question.

For example, the release of fluorescein and BSA were measured using a UV spectrophotometer, Hewlett Packard Vectra XMUV, operating at 280 nm and ambient temperature. The release of gentamicin was measured using standard fluorescense immunoassay methodology (FPIA) and TDX instrumentation. Cefazolin release was monitored using the above-described UV spectrophotometer operating at 272 nm. The results were summarized in Table 1 (supra) and were displayed graphically in FIGS. 1A–1F.

The data from the Figures and Table 1 indicate that controlled release delivery for extended periods can be achieved by using the devices of this invention that are characterized by a ratio of orifice area/total surface area of less than 10%, regardless of the solubility of the drug and the number and configuration of the orifices of the device. The data also indicate that more than one drug can be delivered by the present devices and that the release characteristics of each drug can be influenced by the other. See, Examples 4, 5, and 6, FIGS. 1A–1F and Table 1.

Examples 7–9

Delivery Device Comprising Dexamethasone
(Cylindrical Devices, Varied Orifice Number and Configuration)

By following the procedure described in the case of Examples 1–6 above, cylindrical devices of polyfluorinated ethylenepropylene (FEP) material comprising dexamethasone were prepared. In Example 7, the device had three orifices on the longitudinal surface of the cylindrical device and both the spherical faces of the device are sealed. The device comprised 2.9 mg of dexamethasone. In Example 8, the device comprised of a total of four orifices, one resulting from a spherical face which is left open (i.e., unsealed). Three additional orifices were made on the longitudinal surface of the device as described above. The device comprised of 3.4 mg of dexamethasone. In the case of both Examples 7 and 8, the devices were 7.2 mm long.

In Example 9, the device comprised of a total of two orifices, each one resulting from the spherical face which is left open (i.e., unsealed). The device was 5.2 mm long and comprised of 2.6 mg of dexamethasone.

In the case of Examples 7 and 8, each orifice was spherical and had an internal diameter of 0.5 mm, with a total orifice area/total surface area of 1.884% and 4.104%, respectively. The corresponding figures in the case of Example 9 are 0.94 mm and 5.962%. See Table 1. In all cases, the tubes had an internal diameter of 0.94 mm and an outer diameter of 1.27 mm.

Release Study

The procedure was similar to that as described in Examples 1–6 above. The amounts of dexamethasone released was measured using HPLC, C18 column with a UV detection operating at 280 nm. The data were summarized in Table 1 and displayed graphically in FIG. 2.

The data indicate that regardless of the number and configuration of the orifices in each device, as well as the length of the device, all three devices provided controlled release delivery over a prolonged period, in these cases, from 365 to 455 days. The data support the general conclusion that so long as the orifice area/total surface area of the device is less than 10%, such devices can be used to deliver drugs in a controlled release manner over prolonged periods of time.

Examples 10–13

Delivery Devices Comprising an Aldose Reductase Inhibitor (ARI) (Cylindrical Devices, Varied Orifice Number and Configuration)

By following the procedure described in Example 4 above, cylindrical devices of Teflon® material comprising ARI were prepared. ARI represents a generic groups of compounds known as aldose reductase inhibitors. Such aldose reductase inhibitors are well-known in the art. See, for example Sorbinil. Any of the aldose reductase inhibitors can be used for delivery with the present devices. In Example 10, the device comprised of a total of three orifices, wherein two orifices were created by leaving open each of the spherical face of the cylindrical device. The third orifice was created by a mechanical drill. The device comprised of 2–3 mg of an ARI.

In Example 11, the same procedure as in Example 10 was followed, to create a cylindrical device, except that in this case, the device consisted of four orifices. One orifice was derived from each of the two spherical faces which were left unsealed. Two additional orifices were created on the longitudinal surface of the cylindrical device as described above.

In Example 12, the procedure as in Example 11 was followed to prepare a cylindrical device consisting of a total of five orifices, one from each unsealed spherical face of the device and three on the longitudinal face.

In Example 13, the procedure as in Example 10 was followed to prepare a cylindrical device having two orifices only, wherein one orifice resulted from each of the spherical face which is left open, i.e., unsealed. No additional orifices were created on the longitudinal surface of the cylindrical device.

In all the above Examples (10–13), Teflon® tubes of 0.97 mm internal diameter and 1.31 mm outer diameter were used. The area of each orifice created from each spherical face of the device was 1.48 mm$^2$. Each orifice created on the longitudinal surface (except for the case of Example 13) is spherical and has an internal diameter of 0.5 mm. The length of the tube in case of Examples 10 and 13 was 5.2 mm and in the case of Examples 11 and 12, it was 6.2 mm. The devices had a combined orifice area/total surface area ranging from 6.134% to 7.327%. See Table 1. The amount of drug in each device ranged from 2 mg in Example 10 to 2.2 mg in Example 13 to 2.6 mg each in Examples 11 and 12. The release was measured for 579 days.

Release Study

The procedure was similar to that as described in Example 7 above. The amount of ARI released was measured using HPLC methodology, with a C18 column and a UV detector operating at 280 nm. The data were summarized in a table and graphically displayed in FIG. 3.

These results indicate that controlled release delivery over prolonged periods, in this case, several hundreds of days, can be obtained regardless of the number and configuration of the orifices in the device.

Examples 14–20

Delivery Device Comprising Ganciclovir[9-[[2-hydroxy-1-(hydroxymethyl)ethoxy]-methyl]-guanine (DHPG)](Cylindrical Device with Both Spherical Ends Sealed, Varied Orifice Number)

Small holes were drilled longitudinally in the wall of a silicone tube (Examples 14–19) or a Teflon® tube (Example 20), using an Excimer laser. The silicone devices were prepared as following: a bead of silicone adhesive was injected approximately 1.5 mm into one end of a tube. After the adhesive dried and cured, about 5 mg of DHPG (in case of Examples 14–19) or 50 mg of DHPG (in case of Example 20) was packed into the open end of the tube with a small plunger. The tube was then cut to an appropriate length, leaving 1.5–2.0 mm at the end. A bead of adhesive was injected to seal the open end. The adhesive was allowed to dry and cure before the DHPG delivery system was used.

The Teflon® device for Example 20 was prepared using the procedures described in the case of Example 13 above, but using DHPG, instead of ARI as the drug.

The tube in each case was 10 mm in length. The silicone tubes had an outer diameter of 1.65 mm and an internal diameter of 1.02 mm, whereas the Teflon® tube had an outer diameter of 5 mm and an internal diameter of 3.175 mm. All the silicone tubes had their both spherical faces sealed and two or three orifices were provided on their longitudinal surfaces. The Teflon® tube device on the other hand had its both spherical faces left open, creating the only two orifices of the device.

The diameter of the orifice in the silicone devices varied from 0.125 mm to 0.250 mm. The orifices of the Teflon® device had an internal diameter identical to the tube's internal diameter, namely, 3.175 mm. The ratio of orifice area to the total surface area of the silicone device ranged from 0.044 to 0.262, whereas the corresponding value for the Teflon® device was 8.065. See Table 1. The amount of DHPG in all cases was 5 mg per device, except for in Example 20 where the amount of DHPG was 50 mg.

Release Study

The methodology was as described in the case of Example 5. The amount of DHPG release was measured by HPLC. The data for silicone devices were summarized in Table 2 and displayed graphically in FIG. 4. These data indicate that as the ratio of orifice area to total surface area of the device decreased, the duration of release increased, indicating further that prolonged release can be obtained by lowering the ratio of orifice area to total surface area of the device. The fact that the Teflon(& device, having the greatest ratio under consideration (8.0625%), released the drug very quickly (in about 24 days) further supports this result. Among the silicone devices, the ratio of orifice area/surface area and the release duration appears to be strongly correlated, indicating that as the ratio decreased by half, the duration of release increased roughly by two-fold.

The data show that devices with orifice areas less than 10% of the total surface area of the device, more preferably, less than 1% for silicone devices can deliver drugs for prolonged time.

Example 21

Biodegradable Delivery Device Comprising Polylactic Acid Polymer and Ganciclovir[9-[[2-hydroxy-1-(hydroxymethyl)ethoxy]-methyl]-guanine (DHPG)](Cylindrical Device with Both Spherical Ends Open, One Additional Orifice)

Figure 5:
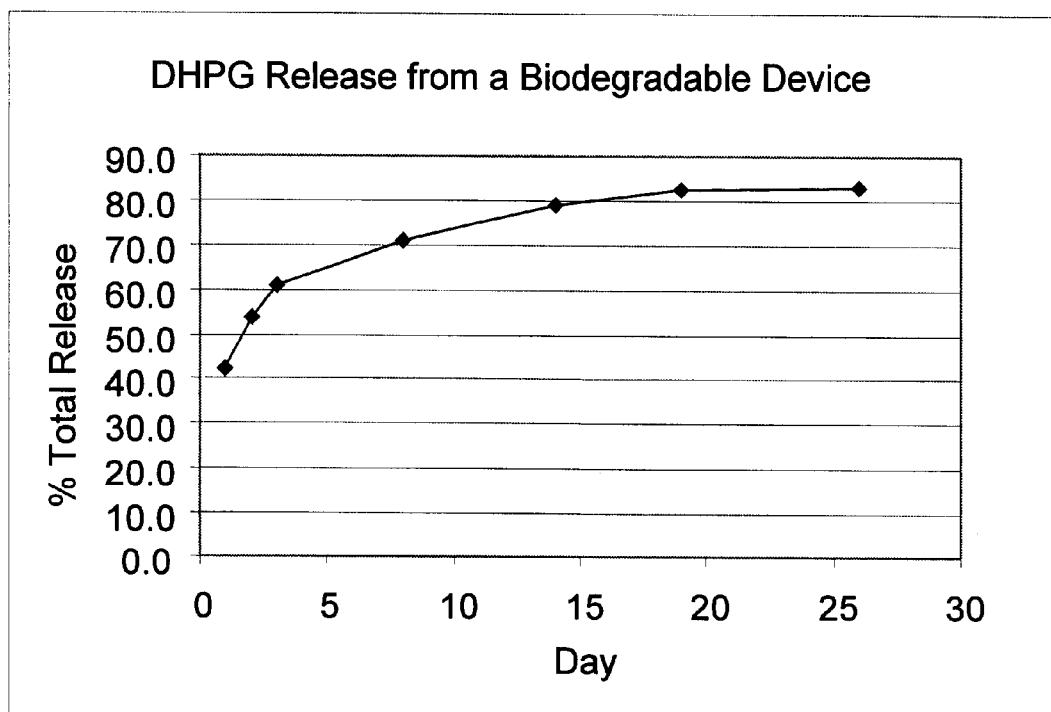
FIG. 5 is a graphical display of ganciclovir[9-[[2-hydroxy-1-(hydroxymethyl)ethoxy]-methyl]-guanine (DHPG)] release data from cylindrical devices made from polylactic acid, wherein each spherical face of the cylindrical device is open and one additional orifice is drilled on the longitudinal surface of the cylindrical device.

Polylactic acid biodegradable delivery devices were prepared by using injection molding process, which has been generally described supra. The device was cylindrical with both spherical ends open and had one orifice on its longitudinal face obtained by a mechanical drill. The total orifice area was less than ten percent of the total surface area of the device. The device comprised of 10.8 mg of DHPG. Release of DHPG from the device was measured as in the above Example. The release data was shown graphically in FIG. 5. The data indicate that biodegradable polymeric devices can deliver drugs at a controlled rate for a prolonged period when the total orifice area is less than ten percent of the surface area of the device.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are intended to be within the fill range of equivalence of the following claims.

We claim:

1. A biocompatible implantable ocular controlled release drug delivery device sized for implantation within an eye for continuously delivering a drug within the eye for a period of at least several weeks comprising a polymeric outer layer that is substantially impermeable to the drug and ocular fluids covering a core comprising a drug that dissolves in ocular fluids, wherein said outer layer has one or more orifices through which ocular fluids may pass to contact the core and dissolve drug and dissolved drug may pass to the exterior of the device, said orifices in total having an area less than one percent of the total surface area of said device, and wherein the rate of release of the drug is determined solely by the composition of the core and the total surface area of the one or more orifices relative to the total surface area of said device.

2. The device of claim 1, wherein said orifices have circular openings with diameters in the range of about 0.001 mm to 0.5 mm.

3. The device of claim 1, wherein said device is cylindrical and has a diameter of about 0.5 and 4 mm and a length of about 3 to 7 mm.

4. The device of claim 1, wherein said outer layer comprises polytetrafluoroethylene, polyfluorinated ethylenepropylene, polylactic acid, polyglycolic acid, or silicone or a mixture thereof.

5. The device of claim 1, wherein said drug is an antibiotic, an antiviral agent, an antifingal agent, an anticancer agent, an antiglaucoma agent, an antiinflammatory agent, an analgesic, an immunomodulatory agent, a macromolecule or a mixture thereof.

6. The device of claim 5, wherein said drug is an antiviral agent that is effective against a cytomegalovirus, a herpes virus, an adenovirus, or a mixture thereof.

7. The device of claim 5, wherein said drug is a cyclosporin, tacrolimus, an interferon, or a mixture thereof.

8. The device of claim 5, wherein said drug is a nucleic acid, a protein, a carbohydrate, a glycoprotein, a lipid, a glycolipid, or a mixture thereof.

9. The device of claim 5, wherein the drug is gentamicin, cefazolin, dexamethasone, aldose reductase inhibitor, ganciclovir, fluocinolone, triamcinolone, fluorometholone, prednisone, prednisolone or a mixture thereof.

10. The device of claim 1, wherein the outer layer is biodegradable.

11. The device of claim 1, wherein the core consists essentially of the drug.

12. The drug delivery device of claim 1, wherein the substantially impermeable outer layer comprises polytetrafluoroethylene, and said drug is gentamicin, cefazolin, or a mixture thereof.

13. The drug delivery device of claim 1, wherein the substantially impermeable outer layer comprises polyfluorinated ethylenepropylene, and said drug is dexamethasone.

14. The drug delivery device of claim 1, wherein the substantially impermeable outer layer comprises polytetrafluoroethylene, and said drug is an aldose reductase inhibitor.

15. The drug delivery device of claim 1, wherein the substantially impermeable outer layer comprises polytetrafluoroethylene, and said drug is 9-[[2-hydroxy-1-(hydroxymethyl)ethoxy]-methyl]-guanine.

16. The drug delivery device of claim 1, wherein the substantially impermeable outer layer comprises polytetrafluoroethylene or silicone or a mixture thereof, and said drug is ganciclovir.

17. The drug delivery device of claim 10, wherein the substantially impermeable biodegradable outer layer comprises polylactic acid, polyglycolic acid, or a mixture thereof, and said drug is ganciclovir.

18. A method of treating or preventing an ocular condition in an eye comprising implanting a biocompatible ocular controlled release drug delivery device of claim 1 within the eye.

19. The device of claim 1, wherein said outer layer has two or more orifices.

* * * * *

UNITED STATES PATENT AND TRADEMARK OFFICE
CERTIFICATE OF CORRECTION

PATENT NO.    : 6,331,313 B1
DATED         : December 18, 2001
INVENTOR(S)   : Vernon G. Wong et al.

It is certified that error appears in the above-identified patent and that said Letters Patent is hereby corrected as shown below:

<u>Title page,</u>
Item [56], References Cited, U.S. PATENT DOCUMENTS:
Reference number 11, "4,201,210 5/1982" should be -- 4,201,210 5/1980 --.

Item [56], References Cited, FOREIGN PATENT DOCUMENTS:
Reference number 2, "WO 94/11244" should be -- WO 99/11244 --.
Reference number 3, "WO 94/62760" should be -- WO 00/62760 --.

<u>Column 2,</u>
Lines 53-54, devices made silicone" should be -- devices made from silicone --.

<u>Column 4,</u>
Line 62, "filmarate" should be -- fumarate --.

<u>Column 11,</u>
Line 5, "foscamet" should read -- foscarnet --.

<u>Column 23,</u>
Line 13, "Teflon(& device" should be -- Teflon® device --.

Signed and Sealed this

Third Day of September, 2002

Attest:

*Attesting Officer*

JAMES E. ROGAN
*Director of the United States Patent and Trademark Office*